United States Patent [19]

Weber et al.

[11] 4,205,013

[45] May 27, 1980

[54] PROCESS FOR THE MANUFACTURE OF 2,3-DIMETHYLPENTANAL

[75] Inventors: Jürgen Weber, Oberhausen; Helmut Springer, Voerde, both of Fed. Rep. of Germany

[73] Assignee: Ruhrchemie Atkiengesellschaft, Oberhausen, Fed. Rep. of Germany

[21] Appl. No.: 891,380

[22] Filed: Mar. 28, 1978

[30] Foreign Application Priority Data

Apr. 13, 1977 [DE] Fed. Rep. of Germany ....... 2716288

[51] Int. Cl.² ............................................. C07C 45/10
[52] U.S. Cl. .................................................. 568/451
[58] Field of Search ..................... 260/604 H, 604 HF

[56] References Cited

U.S. PATENT DOCUMENTS

| 3,081,357 | 3/1963 | Alderson | 260/604 HF |
|---|---|---|---|
| 3,636,034 | 1/1972 | Ohsumi et al. | 260/604 HF |
| 3,755,393 | 8/1973 | Kniese | 260/604 HF |

OTHER PUBLICATIONS

Stefani et al., "J.A.C.S.", vol. 95 No. 19, pp.6504–6505 (1973).
Pino et al., "Chemistry & Industry" (Feb. 1963), pp. 294–295, TPI-563.

*Primary Examiner*—Werren B. Lone
*Attorney, Agent, or Firm*—Sprung, Felfe, Horn, Lynch & Kramer

[57] ABSTRACT

A process for the preparation of 2,3-dimethylpentanal which comprises contacting 3-methyl-2-pentene with carbon monoxide and hydrogen in the presence of a rhodium carbonyl compound as catalyst. Rhodium carbonyl catalysts are those which contain only rhodium and carbon monoxide and in certain cases, also hydrogen. Especially contemplated are non-phosphine containing rhodium carbonyl catalysts.

8 Claims, No Drawings

PROCESS FOR THE MANUFACTURE OF 2,3-DIMETHYLPENTANAL

BACKGROUND OF THE INVENTION

1. Field of the Invention

This invention relates to a process for the preparation of 2,3-dimethylpentanal. More especially, this invention relates to an improved process for the preparation of 2,3-dimethylpentanal via hydroformylation of 3-methyl-2-pentene employing a rhodium carbonyl catalyst. The catalyst employed according to the process of the invention is one consisting essentially of rhodium, carbon monoxide and in certain cases, hydrogen.

1. Discussion of the Prior Art

According to the process described in U.S. Pat. No. 3,359,324, 2,3-dimethylpentanal can be manufactured from crotonaldehyde. The synthesis is multi-stage. Crotyl alcohol, propionaldehyde dicrotyl acetal and 1-propenyl-crotyl ether result as intermediate compounds.

The reaction of methyl sec-butyl ketone with monochlorodimethyl ether to 1-methoxy-2,3-dimethyl-2-pentanal and the subsequent hydrolysis of the methoxyaldehyde with hydrochloric acid also result in 2,3-dimethylpentanal (French Pat. No. 1,377,141).

The manufacture of 2,3-dimethylpentanal via hydroformylation of 3-methyl-1-pentene is described by P. Pino et al in "Chemistry and Industry", 1963, p. 294. When cobalt carbonyl is employed as catalyst, a reaction product containing 93% 4-methylhexanal but only 3% 2,3-dimethylpentanal is obtained.

With the hydroformylation of 3-methyl-2-pentene in the presence of hydridocarbonyltris (triphenylphosphine) rhodium, a reaction product with an 85–86% 2,3-dimethylpentanal content is obtained with a 50% olefin conversion. (Stefani et al, Journal of American Chemical Society, 95: 19, 6504, 1973).

Consequently, the known processes for the synthesis of 2,3-dimethylvaleraldehyde require either a multi-stage procedure or they result, in the case of less complex reactions, in unsatisfactory yields of the required compound. The application of rhodium carbonyls (containing phosphine) is confronted by the high cost of this catalyst, as its separation in undecomposed form from the reaction product is highly involved. Moreover, the olefin conversion with this special catalyst system is very small.

It is an object of this invention, therefore, to provide a process for the economical preparation of 2,3-dimethylpentanal. More especially, it is an object of this invention to provide an economical process by which 2,3-dimethylpentanal can be prepared on an industrial scale through the hydroformylation of 3-methyl-2-pentene. It is a further object of this invention, therefore, to provide an improved process for the hydroformylation of 3-methyl-2-pentene by which high yields of 2,3-dimethylpentanal are realized. These and other objects of this invention will become apparent from the following description and claims.

SUMMARY OF THE INVENTION

This invention contemplates an improvement in a process for the manufacture of 2,3-dimethylpentanal by hydroformylating 3-methyl-2-pentene with carbon monoxide and hydrogen employing a rhodium containing catalyst, the improvement residing in employing as the catalyst a rhodium carbonyl catalyst. By the term "rhodium carbonyl catalyst" it is to be understood herein that the catalyst consists essentially of rhodium, carbon monoxide and in certain cases, also hydrogen. Preferably, the rhodium carbonyl catalyst employed in accordance with the claimed process is a non-phosphine containing rhodium carbonyl catalyst.

Surprisingly, it was found in contrast to the opinion in professional circles (cf. e.g. Fell et al, Tetrahedron Letters, No. 29, p. 3261, 1968) that an isomerization of the olefin feed, when rhodium carbonyl compounds are employed as hydroformylation catalysts, occurred only to a minor extent. The rhodium carbonyl catalysts used in accordance with the invention are very effective even in small concentrations, in contrast to the rhodium carbonyl compounds containing phosphine.

For good results, rhodium concentrations of 10 to 1000 ppm, relative to the 3-methyl-2-pentene feed should be used. Rhodium concentrations of 50 to 200 ppm are preferably employed.

The separation of the unmodified rhodium carbonyl from the reaction mixture, once again in contrast to the rhodium carbonyl phosphine complexes, is extremely simple and can be carried out according to the known methods, e.g. through adsorption on solids with large surface areas, the treatment of the crude oxo product with steam, halogens or carboxylic acids.

The reaction of the olefin with carbon monoxide and hydrogen is usually carried out at temperatures between 70° and 150° C., preferably between 90° and 110° C. and at pressures of 200 to 400 bar, preferably 250 to 320 bar. Carbon monoxide and hydrogen are employed in the mol ratio 3:1 to 1:3, preferably 1:1. The reaction can take place either in the presence or absence of a solvent. Cyclohexane, toluene, tetrahydrofuran as well as other inert organic solvents are suitable as solvents. In order to obtain pure 2,3-dimethylpentanal from the catalyst-free aldehyde mixture, resulting at the reaction, it can, for example, be distilled in high vacuum. 2,3-Dimethylpentanal is a valuable feedstock for the manufacture of tranquilizers, hypotensors and soporifics.

In order to more fully illustrate the nature of the invention and the manner of practicing the same, the following examples are presented.

EXAMPLE 1

400 g of 3-methyl-2-pentene as well as 40 mg Rh (in the form of 2-ethylhexanoate) were introduced into a high pressure vessel (volume 2.1 liters) and were reacted with an equimolar mixture of carbon monoxide and hydrogen at 90° C. and 260–270 bar. The reaction was completed in 7 hours, after which the pressure was relieved and the reactor allowed to cool. The composition of the crude reaction product was determined by a vacuum distillation and a gas chromatographic analysis. With a 99.9% 3-methyl-2-pentene conversion, 81.3% of isomeric $C_7$ aldehydes was obtained as 2,3-dimethylpentanal (cf. Table 1, Exp. 1).

EXAMPLES 2–4

As in Example 1, 400 g of 3-methyl-2-pentene in the presence of Rh are hydroformulated each time under various reaction conditions in a high pressure vessel with a volume of 2.1 liters. The resulting yields are also illustrated in Table 1.

Table 1:

Hydroformylation of 3-Methyl-2-pentene using Rhodium
(in the form of 2-ethylhexanoate)

| Exp. No. | Rhodium Content (ppm) | Reaction Temp. (°C.) | Reaction Pressure (bar) | Yields: from 100 g 3-methyl-2-pentene the following is obtained (in g) | | | | | Reaction Time (hours) |
|---|---|---|---|---|---|---|---|---|---|
| | | | | Olefins | 2,3-Dimethyl-pentanal | 3-Ethyl-pentanal | 4-Methyl-hexanal | Miscell-aneous | |
| 1 | 100 | 90 | 270 | 0.1 | 108.5 | 3.7 | 21.3 | 1.9 | 7.0 |
| 2 | 100 | 80 | 270 | 9.4 | 103.8 | 2.2 | 16.3 | 0.5 | 7.5 |
| 3 | 100 | 100 | 270 | — | 102.0 | 3.8 | 27.6 | 2.0 | 5.5 |
| 4 | 1000 | 90 | 270 | 0.1 | 110.5 | 3.5 | 19.4 | 2.0 | 5.0 |

We claim:

1. In a process for the preparation of 2,3-dimethylpentanal by hydroformylation of 3-methyl-2-pentene with carbon monoxide and hydrogen in the presence of a rhodium containing catalyst at an elevated temperature and pressure and at a time sufficient to produce 2,3-dimethylpentanal, the improvement wherein said rhodium containing catalyst is a non-phosphene rhodium carbonyl catalyst.

2. A process according to claim 1 wherein the hydroformylation is carried out at a temperature of 70° to 120° C. at a pressure of 200 to 400 bar.

3. A process according to claim 1 wherein the rhodium concentration is 10 to 1000 ppm.

4. A process according to claim 3 wherein the rhodium concentration is 50 to 200 ppm.

5. A process according to claim 1 wherein the process is carried out in the presence of carbon monoxide and hydrogen which are employed in a mol ratio of 3:1 to 1:3.

6. A process according to claim 1 wherein said rhodium carbonyl catalyst contains carbon monoxide.

7. A process according to claim 6 wherein said rhodium carbonyl catalyst additionally contains hydrogen.

8. In a process for the preparation of 2,3-dimethylpentanal by hydroformylation of 3-methyl-2-pentene with carbon monoxide and hydrogen in the presence of a rhodium catalyst at an elevated temperature and pressure and at a time sufficient to produce 2,3-dimethylpentanal, the improvement wherein said rhodium catalyst is rhodium-2-ethyl-hexanoate.

* * * * *